United States Patent [19]

Ahle

[11] 4,066,439
[45] Jan. 3, 1978

[54] METHOD OF SELECTIVELY COMBATING WILD OATS

[75] Inventor: James L. Ahle, Shawnee Mission, Kans.

[73] Assignee: Gulf Oil Corporation, Pittsburgh, Pa.

[21] Appl. No.: 625,233

[22] Filed: Oct. 23, 1975

[51] Int. Cl.$^2$ ............................................. A01N 9/20
[52] U.S. Cl. ................................. 71/111; 71/DIG. 1
[58] Field of Search .......................................... 71/111

[56] References Cited

U.S. PATENT DOCUMENTS

| 2,695,225 | 11/1954 | Witman | 71/111 |
|---|---|---|---|
| 3,892,556 | 7/1975 | Stobbe | 71/111 |

FOREIGN PATENT DOCUMENTS

| 963,355 | 7/1964 | United Kingdom | 71/111 |
|---|---|---|---|
| 1,186,472 | 4/1970 | United Kingdom | 71/111 |

OTHER PUBLICATIONS

Wiese et al., "Fall Applications of IPC & CIPC etc.;" (1954), CA 49, p. 5754, (1955).
Nowak, "Effect of the Preparation Aaservo etc.," (1974), CA 82, No. 154,000e, (1975).

*Primary Examiner*—Glennon H. Hollrah
*Attorney, Agent, or Firm*—Carl A. Cline

[57] ABSTRACT

Wild oats are killed over a substantial period of growth from two-leaf through four-leaf stages by applying post-emergently to the oats plants an effective amount of a combination of one part of barban with from about two to five parts, preferably three to four parts of CIPC, a herbicide which is normally applied pre-emergently.

3 Claims, No Drawings

METHOD OF SELECTIVELY COMBATING WILD OATS

DESCRIPTION OF THE INVENTION

Background

Wild oats are widely distributed weeds which present serious problems primarily in the cooler wheat-growing areas of both North America and Europe. Moderate infestations can reduce wheat yields by 25 to 30 percent. Selective control of wild oats in the presence of growing crops such as wheat or barley is so difficult that in spite of vigorous efforts on the part of farmers, wild oat infestations have become worse during the last decade. The oats in general are less sensitive to herbicides than either wheat or barley, so that selective control is possible with only a very few herbicides and only during a brief period in the growth and development of the wild oats plants.

A commonly used wild oat herbicide is 4-chloro-2-butynyl m-chlorocarbanilate (barban) which is normally sprayed post-emergently shortly after the wild oats have emerged and have no more than two leaves. At this stage of growth the oats are more sensitive than wheat or barley to barban and good control can be achieved without substantial crop injury. However, weed seeds are not located in the soil at a constant, controlled depth, as are the seeds of a planted crop. Consequently, weeds such as wild oats do not all germinate at the same time and at any time selected for spraying, wild oats are present in various stages of growth. Normally, either plants that are beyond the one-to-two leaf stage or those that are not yet fully emerged will survive and become pests as the wheat or barley matures. Increasing the application rate is not advisable because of the likelihood of injury to the crop plants. It is the customary practice to spray with barban before any of the wild oats plants have reached the three-leaf stage, leaving only the later-germinating oats plants to compete with the wheat. If weather permits spraying at exactly the right time about 80 percent control is achieved and reduction of wheat yield is substantially prevented. However, late-germinating wild oats then re-seed the field, so that the degree of weed infestation remains relatively constant from year to year.

Summary of Invention

Briefly, I have discovered that a combination of one part of barban with from about two to five parts of isopropyl m-chlorocarbanilate (CIPC) may be used to selectively kill wild oats in the two to four-leaf stages of growth in the presence of wheat or barley. The preferred rates of application of the two herbicides in wheat are 2 oz. of barban along with 6 to 8 oz. of CIPC per acre. The two herbicides may be applied by spraying separately or preferably by spraying an aqueous dispersion containing both compounds. Higher rates of application may be preferred for combating wild oats in the presence of other crops such as sugar beets, or when adverse weather conditions have caused growth to be slow.

Detailed Description

Barban is a compound of very high phytotoxicity and is therfore customarily applied at very low application rates, usually about 4 to 6 oz. per acre in the field. The wild oats plants are small, often present in numbers of about 10 to 50 per square foot. As the plants occupy a small percentage of total area and only about 5 gallons of spray mixture are applied to an acre, it will be understood that uniform application of a large number of drops is necessary in order to insure that each plant will receive an adequate amount of herbicide. This is customarily accomplished by proper selection and calibration of spray nozzles and use of a sprayer pressure of at least 45 psi. The conventional application techniques should also be employed with the herbicide combinations employed in the method of this invention, so as to insure uniform distribution of the herbicides.

In general, warm weather, average or better moisture and good soil fertility produce rapid growth of wild oats plants so that they reach the two to four-leaf stage in a shorter period of time and are more susceptible to injury by the herbicide combination employed in the method of this invention. Wild oats plants which have grown more slowly under less favorable conditions are more resistant. Rate of application must therefore be adjusted to some extent to compensate for the growing conditions in the particular field. In the greenhouse experiments described below, ideal conditions for rapid growth were maintained. The uniformity of conditions assured more valid comparisons and maintenance of optimum growth conditions resulted in most economical use of both chemicals and time.

Greenhouse Experiments

Wild oats and wheat were planted in greenhouse potting soil in separate polystyrene foam pots four inches in diameter, the wild oats being planted about 4 days earlier than the wheat, so that all of the plants would reach the three to four-leaf stage of growth at approximately the same time.

The barban and CIPC were first formulated as water-dispersible concentrates by use of suitable solvents and surface active agents. The proper proportions of dispersible concentrate were then mixed with water to form spray mixtures, which were applied with a No. 650017 spray nozzle at a spray volume of 10 gal per acre.

A preferred dispersible formulation is the following:

| | Ingredients | Quantity |
|---|---|---|
| Herbicides | barban | 1 part by weight |
| | CIPC | 3 to 4 parts by weight |
| Solvent | (Mixture of aromatic petroleum distillate and alkyl benzenes) | 10 to 12 parts by weight |
| Surfactant | (Commercial emulsifier mixture of anionic and non-ionic surfactants) | Amount sufficient to disperse the formulation in water. |

The potted wheat and wild oats plants were sprayed at the 3 to 3.5 leaf stage, about 9 to 11 inches in height, as described above, all experiments being conducted in duplicate. The results were evaluated within 3 to 4 weeks after spraying on a scale of from 0 (no effect) to 10 (total control). Results are tabulated below.

| Application Rate in oz./A | | Wild Oats | | Wheat | |
|---|---|---|---|---|---|
| barban | CIPC | Rep 1 | Rep 2 | Rep 1 | Rep 2 |
| 2 | 8 | 10 | 10 | 0 | 0 |
| 1 | 4 | 10 | 9 | 0 | 0 |
| 2 | 4 | 6 | 8 | 0 | 0 |
| 0 | 8 | 5 | 4 | 0 | 0 |
| (1) 8 | 0 | 7 | 8 | 2 | 2 |

-continued

| Application Rate in oz./A | | Wild Oats | | Wheat | |
|---|---|---|---|---|---|
| barban | CIPC | Rep 1 | Rep 2 | Rep 1 | Rep 2 |
| (1) 4 | 0 | 3 | 5 | 0 | 0 |

(1) Commercial formulation.

In experiments in wheat fields in which the majority of wild oats were beyond the 2 leaf stage of growth, barban and CIPC were applied in various proportions by mixing separate dispersible concentrates of the two herbicides with water in the spray tank. Results were scored in the same manner as the greenhouse tests and yields were measured at harvest. The data are tabulated below.

| Application rate in oz./A | | Wild oats | Durum Wheat (Rolette variety) | |
|---|---|---|---|---|
| barban | CIPC | Injury Mean score | Injury Mean score | Yield bu/A |
| 2 | 8 | 6.7 | 0.3 | 15.6 |
| 4 | 0 | 6.0 | 0.0 | 13.3 |
| 6 | 0 | 5.3 | 3.3 | 9.6 |
| 3 | 3 | 6.0 | 2.3 | 9.6 |
| 3 | 6 | 4.7 | 3.3 | 9.1 |
| 0 | 16 | 0.0 | 0.7 | 8.5 |
| 0 | 0 | 0.0 | 0.0 | 5.8 |

It will be seen from these results that the combination of barban with CIPC, besides being effective on older wild oats plants can also be used at higher application rates to give equivalent or better control of wild oats with less injury to wheat than barban alone. It may also be seen from these results that CIPC, when used alone, even at 1 lb per acre is relatively ineffective with respect to either wild oat control or wheat injury (Some improvement of wheat yield may result from control of other weed species.) When the combinations of barban and CIPC are used in fields in which wild oats vary in growth from the one-leaf to the 4-leaf stage, satisfactory control of the entire wild oat population is obtained, so that maximum yields of wheat result, as well as a significant reduction of overall wild oat infestation from one growing season to the next. When combinations of barban with CIPC are used to control wild oats in barley fields there is less danger of crop injury, so that higher application rates may be used, if increased control of wild oats is desired.

I claim:

1. The method of selectively killing wild oats plants in stages of growth varying from the two-leaf to four-leaf stage in the presence of wheat or barley comprising applying to said wild oats plants an effective amount of a combination of one part of barban, from two to five parts of CIPC and an inert diluent.

2. The method of selectively killing wild oats plants in stages of growth varying from the two-leaf to four-leaf stage in the presence of wheat or barley comprising applying to said wild oats plants an aqueous dispersion of barban and CIPC at a rate of 2 oz. of barban and 6 to 8 oz. of CIPC per acre.

3. A composition for selective control of wild oats in the presence of wheat or barley comprising an effective amount of a mixture containing one part by weight barban, 3 to 4 parts by weight CIPC, 10 to 12 parts by weight of a solvent mixture containing aromatic petroleum distillate and alkylbenzenes and a sufficient amount of a commercial emulsifier mixture of anionic and non-ionic surfactants to disperse said composition in water.

* * * * *